United States Patent [19]

Peterson

[11] Patent Number: 5,730,933
[45] Date of Patent: Mar. 24, 1998

[54] RADIATION STERILIZATION OF BIOLOGICALLY ACTIVE COMPOUNDS

[75] Inventor: Dale R. Peterson, Carmel, Ind.

[73] Assignee: DePuy Orthopaedics, Inc., Warsaw, Ind.

[21] Appl. No.: 633,032

[22] Filed: Apr. 16, 1996

[51] Int. Cl.$^6$ .................................................. A61L 2/08
[52] U.S. Cl. ............................................ 422/22; 425/549
[58] Field of Search ............................... 422/22–24, 40; 424/549, 543

[56] References Cited

U.S. PATENT DOCUMENTS

| | | | |
|---|---|---|---|
| 1,676,579 | 7/1928 | Sperti et al. | |
| 3,016,336 | 1/1962 | Scott et al. | 195/63 |
| 3,645,849 | 2/1972 | Gray | 424/101 |
| 4,250,139 | 2/1981 | Luck et al. | 422/21 |
| 4,440,750 | 4/1984 | Glowacki et al. | 424/95 |
| 4,460,445 | 7/1984 | Rekers | 204/159.2 |
| 4,620,908 | 11/1986 | Van Duzer | 422/22 |
| 4,645,503 | 2/1987 | Lin et al. | 623/16 |
| 4,727,027 | 2/1988 | Wiesehahn et al. | 435/173 |
| 4,902,508 | 2/1990 | Badylak et al. | 424/95 |
| 4,956,178 | 9/1990 | Badylak et al. | 424/551 |
| 5,283,034 | 2/1994 | Okrongly et al. | 422/22 |

OTHER PUBLICATIONS

Callegaro, L. et al., Hollow Fiber Immobilized L–asparaginase: in vivo and in vitro Immunological Studies, The International Journal of Artificial Organs, vol. 6, No. 2, pp. 91–96, Mar. 1983.

Farrell, J. Paul et al., Selecting a Radiation Sterilization Method, Medical Device & Diagnostic Industry, pp. 82–90 (Aug. 1995).

Ijiri, S. et al., Influence of Sterilization on Bone Morphogenetic Protein, Fourth World Biomaterials Congress, pp. 21, Apr. 24–28, 1992.

Ijiri, S. et al., Effect of Sterilization on Bone Morphogenetic Protein, Journal of Orthopaedic Research, vol. 12, pp. 628–636, 1994.

Puolakkainen, P.A. et al., The Effect of Sterilization on Transforming Growth Factor β Isolated from Demineralized Human Bone, Transfusion, vol. 33, No. 8, pp. 679–685, 1993.

Schmitz, John P. et al., Characterization of Rat Calvarial Nonunion Defects, Acta Anat 138:185–192, 1990.

Woolston, John, Irradiation Sterilization of Medical Devices, Medical Design and Material, pp. 42–51, Jan. 1991.

*Primary Examiner*—Thomas G. Wyse
*Attorney, Agent, or Firm*—Barnes & Thornburg

[57] ABSTRACT

The present invention relates to a composition and method that optimizes retention of physiological activity of a biologically active compound during sterilization of said compound with gamma or electron-beam radiation. The method comprises the steps of forming a protected mixture that comprises the biologically active compound, an extraneous protein, and a free-radical scavenger, and irradiating the protected mixture with about 1 to about 3 mRad of gamma or electron-beam radiation.

18 Claims, No Drawings

RADIATION STERILIZATION OF BIOLOGICALLY ACTIVE COMPOUNDS

FIELD OF THE INVENTION

The present invention relates to a method for sterilizing biologically active compounds, more particularly the present invention relates to a method for sterilizing biologically active biopolymers with gamma or electron-beam radiation without significantly affecting the physiological usefulness of the biopolymers.

BACKGROUND AND SUMMARY OF THE INVENTION

Bone defects and bony segment fixation are often repaired by autografts or banked bone. Autografts have a good ability to unify the bone. In fact, physicians often prefer to use bone from sources such as the iliac crest. While clearly osteogenic, using autografts presents several drawbacks. First, autografts require a separate harvest operation, which results in increases in operative time and the use of blood transfusions. Secondly, patients often lack adequate amounts of material for harvesting and are at an increased risk of donation site morbidity. Implantation of banked bone does not require the harvest operation, but its bone healing capability is not as high as that of the autograft. Therefore, it is undesirable to use banked bone in severe conditions such as nonunion.

Over the years, researchers have searched for methods for promoting bone growth without necessitating autografts or banked bones. For example, since the mid-1960's the osteoinductive activity of both demineralized bone matrix (DBM) and bone morphogenetic protein (BMP) has been studied. See, for example, S. Ijiri, *Influence of Sterilization on Bone Morphogenetic Protein*, Forth World Biomaterials Congress, Apr. 24-28, (1992). In addition to DBM and BMP, many compounds possess biological activity and find wide use in medical applications such as prosthetic devices, drugs, blood components, and the like.

Since biologically active compounds can often act as a nutrient source, they are particularly susceptible to contamination with microorganisms, such as bacteria, fungi, viruses, and the like. Therefore, when biologically active compounds are to be introduced into a mammal by ingestion, implantation, injection, etc., it is important that they be substantially free of these contaminating microorganisms.

It is often difficult to sterilize biologically active compounds since the chemical, physical or physiological properties of active compounds are often significantly altered by variations in the compounds' surrounding environment. For example, changes in pH, ionic strength, or temperature can result in reversible or irreversible changes in the character of compounds. Researchers have attempted to avoid irreversible changes to active compounds during sterilization by using ethylene oxide. However, ethylene oxide often reacts with proteins. In addition, because of the known tissue toxicity and the carcinogenic potential of the by-products of ethylene oxide, the Food and Drug Administration has set maximum residue limits for ethylene oxide and it major reaction products ethylene glycol and ethylene chlorhydrin.

Unlike ethylene oxide, radiation sterilization has the advantages of high penetrating ability, relatively low chemical reactivity, and instantaneous effects without the need to control temperature, pressure, vacuum, or humidity. Radiation sterilization is widely used in industry for a variety of products and both dosage levels and its biological effects are well known. It is generally agreed that electron-beam and gamma sterilization are equally effective in killing microbial organisms. While sufficient to effectively kill microorganisms, the radiation generally alters the structure of proteins, DNA, RNA, etc. as to render it biologically inactive. Therefore there remains a significant need for a simple way to effectively and safely sterilize biologically active compounds without deleteriously affecting their chemical, physical, or physiological properties.

One object of the present invention is to provide a method for sterilizing biologically active compounds in a manner that promotes retention of the biological activity of said compounds.

Another object of the present invention is to provide a method for sterilizing biologically active biopolymers using irradiation and preserving at least a portion of the biological activity of said biopolymers.

Yet another object of the present invention is to provide a method for sterilizing medical devices that comprise a biologically active biopolymer using gamma or electron-beam radiation and preserving at least a portion of the biological activity of the biopolymer.

Still another object of the present invention is to provide a method of sterilizing biologically active proteins using either gamma or electron-beam radiation and preserving at least 10 percent of the biological activity of said proteins.

Yet another object of the present invention is to provide a composition that protects biologically active compounds from gamma or electron-beam radiation.

According to the present invention a method for sterilizing biologically active compounds while optimizing retention of their physiological activity is provided. The method comprises the steps of forming a mixture that comprises the biologically active compound and an extraneous protein and cooling the mixture to a temperature sufficient to substantially freeze and immobilize the mixture. The frozen mixture is then irradiated with gamma or electron-beam irradiation for a time sufficient to substantially sterilize the biologically active compound. Preferably, the mixture is irradiated with about 1 to about 3 mRad of gamma or electron-beam radiation.

In another embodiment of the present invention, a method is provided for sterilizing a composition that comprises a biologically active biopolymer with gamma or electron-beam radiation while preserving at least 10 percent of the activity of the biopolymer in the composition. The method comprises the steps of forming a protected mixture that comprises the biologically active biopolymer, an extraneous protein, and a free-radical scavenger. The protected mixture is then irradiated with about 1 to about 3 mRad of gamma or electron-beam radiation.

In yet another embodiment of the present invention, a biologically active composition that exhibits an initial biological activity prior to radiation exposure of about 1 to about 3 mRad of gamma or electron-beam radiation and that retains at least 10 percent of the initial biological activity following such irradiation is provided. The composition comprises a protected mixture including about $10^{-5}$ to about 2.5 weight percent of biologically active compound, about 1 to about 70 weight percent of at least one extraneous protein, and about 0.01 to about 10 weight percent of a free-radical scavenger.

Additional objects, features, and advantages of the invention will become apparent to those skilled in the art upon consideration of the following detailed description and preferred embodiments exemplifying the best mode of carrying out the invention as presently perceived.

DETAILED DESCRIPTION OF THE INVENTION

In accordance with the present invention, a wide variety of biologically active compounds finding use in the treatment of mammals, may be decontaminated or sterilized without significantly affecting the compounds physiological properties. The biologically active compounds are decontaminated with gamma or electron-beam radiation following treatment with an extraneous protein and a free-radical scavenger to form a protected mixture. The protected mixture is irradiated under conditions that inactivate any pathogenic microorganisms, viruses, and polynucleotide fragments thereof, DNA or RNA, whether single or double stranded present within the mixture. At the same time, the protected mixture retains at least a useful portion of the physiological activity of the biologically active compounds.

As used throughout the specification and claims, the term "microorganisms" comprises (1) prokaryotic, eukaryotic and viral microorganisms containing nucleic acids (either DNA or RNA), and (2) nucleic acid genome or sub-genomic fragments from microorganisms. Illustrative viruses comprise: adenovirus, arenavirus, bacteriophage, bunyavirus, hepatitis viruses, including types A, B and non-A, non-B (also designated type C), herpesvirus, retroviruses such as human T-lymphtropic viruses (HTLV), including HTLV types I, II and III, orthomyxovirus, papovavirus, paramyxovirus, picornavirus, poxvirus, reovirus, rhabdovirus, and togavirus. Additional pathogenic microorganisms comprise bacteria, chlamydia, mycoplasma, protozoa, rickettsia and other unicellular microorganisms. The present sterilization method will also be effective against uncharacterized infectious agents that contain nucleic acids, either DNA or RNA.

Various biologically active compositions are capable of undergoing sterilization in accordance with the method of the present invention. A biologically active composition affects the living cells in its surrounding environment. It is necessary that the composition exhibits an initial biological activity prior to radiation exposure. The biologically activity is provided by a biologically active compound that is preferably a biologically active biopolymer. Suitable biologically active biopolymers may be extracted from whole blood, packed red cells, platelets, plasma (fresh or fresh frozen plasma), serum, skin, bone, cartilage, tendon, microorganisms, synthetic proteins, etc., or may be manufactured using recombinant DNA processes. Suitable proteins can be any one of a wide variety of classes of proteins, such as keratins, collagens, albumins, globulins, hormones, enzymes, or the like. The biopolymer can be selected from simple peptides, simple proteins, or conjugated proteins, such as glycoproteins, mucoproteins, lipoproteins, heme proteins, nucleoproteins, or the like. The significant factor is that the biopolymer has chemical and physical properties that are important to its physiological function. Therefore, when sterilizing biologically active compounds, it is essential the compounds' properties be substantially unchanged so as to retain at least a useful portion of physiological function.

Preferably, biologically active compositions preferred for use in the present invention are growth factors, growth factor binding proteins or cells. Examples of suitable growth factors comprise: a fibroblast growth factor, a transforming growth factor (e.g., TGF-$\beta_1$), a bone morphogenetic protein, epidermal growth factor or a platelet-derived growth factor.

Examples of growth factor binding proteins are insulin-like growth factor binding proteins (IGFBP's) such as IGFBP's 3 and 5. Examples of suitable cells comprise bone marrow cells and mesenchymal stem cells. The biologically active composition can also be an osteogenic agent that stimulates or accelerates generation of bone upon implantation into a bone defect site. Examples of osteogenic agents comprise demineralized bone powder, morselized cancellous bone, aspirated bone marrow, bone or cartilage forming cells, and other bone sources.

In order to preserve the physiological activity of biologically active compounds during radiation sterilization, it is necessary to incorporate the compounds into a protected mixture. The amount of biologically active compounds present in a biologically active composition may vary widely ($10^{-5}$ to about 99 percent by weight of the protected mixture) depending upon the biologically active compounds selected. For example, TGF-$\beta_1$ may be present in an amount of about $10^{-5}$ to about 2.5 percent by weight of the protected mixture, more preferably about $10^{-4}$ to about $10^{-3}$ percent by weight. However, allogenic bone graft may be present in the protected mixture in an amount of about 50 to about 99 percent by weight, and more preferably about 80 to about 99 percent by weight.

The protected mixture also comprises an extraneous protein. Suitable extraneous proteins may be selected from proteins such as, for example, gelatin and bovine serum albumin. The amount of extraneous protein present in the protected mixture may vary widely (1 to about 75 weight percent of the mixture) depending upon the biologically active compound selected. For example, when TGF-$\beta_1$ is the biologically active compound, the extraneous protein is about 1 to about 75 percent by weight of the protected mixture. However, when demineralized bone matrix is the biologically active compound, the extraneous protein is about 1 to about 10 percent by weight of the protected mixture.

The protected mixture of the present invention, further comprises a free-radical scavenger. Scavengers suitable for use comprise antioxidants such as tocopherol, citric acid, butylated hydroxyanisole, butylated hydroxytoluene, tertiary butylhydroquinone, propyl gallate, ascorbate, and other antioxidants that are "generally recognized as safe" by the Food and Drug Administration. The amount of free-radical scavenger present within the mixture depends upon the amount of biologically active compound and the extraneous protein used. For example, when TGF-$\beta_1$ is the biologically active compound, the protected mixture preferably comprises about 0.01 to about 10 weight percent of the free-radical scavenger. More preferably, the mixture comprises about 0.1 to about 5 weight percent of the free-radical scavenger.

The protected mixture once formed, is quickly cooled to inhibit denaturation of the biologically active compound. The protected mixture is cooled by flash freezing to about −70° C. However, it is understood that the temperature of the protected mixture may be reduced using various refrigeration techniques. Preferably, the mixture is frozen so that it is substantially immobilized.

The protected mixture is subjected to gamma or electron-beam radiation under standard sterilization conditions. These standard conditions are at an intensity and for a time duration sufficient to destroy substantially all of the microorganism contamination in the biologically active compound. Preferably, the amount of radiation applied to the biologically active compound is relatively constant during the radiation period. The protected mixture is subjected to about 1 to about 3 mRad of gamma radiation, preferably about 2 to about 3 mRad of gamma radiation, and most preferably to about 2.5 mRad of gamma radiation. However, in an alternative embodiment, the protected mixture is subjected to about 1 to about 3 mRad of electron-beam radiation, preferably about 2 to about 3 mRad of electron-beam radiation, and most preferably about 2.5 mRad of electron-beam radiation.

It is understood that biologically active compounds may be effectively sterilized by either gamma or electron-beam radiation. The reason that the sources of radiation may be interchanged is that both gamma rays and electrons interact with matter by electrical ionization and excitation reactions. The mechanisms of the interactions of the gamma rays and electrons, however are different. It is well known that gamma rays are electromagnetic waves frequently referred to as photons. Having no electric charge or mass, photons transfer energy to materials mainly through Compton scattering and, at low energies, through photoelectric absorption. In contrast to gamma rays, electrons have both mass and charge, so they interact readily with other charged particles, transferring their kinetic energy to materials via numerous elastic and inelastic collisions. Therefore, circumstances do exist where one or the other type of irradiation source is preferred. For example, gamma sterilization is often preferred when the bulk density of the material is high or when high-density regions may shield other parts of the material from exposure to electrons.

In an alternative embodiment of the present invention, prior to irradiation, the protected mixture is subjected to vacuum or an inert gaseous atmosphere such as nitrogen, argon, helium, neon, and the like. It has been found that the stability of the biologically active compound improves when subjected to an inert or less reactive gases during irradiation treatment. Preferably, the protected mixture is exposed to a vacuum, nitrogen, or argon atmosphere.

The protected mixture may be immobilized upon a solid substrate. Non-limiting examples of substances suitable for use in accordance with the present invention comprise surfaces much like that in the body where TGF-$\beta_1$ is normally stably bound. In particular, particulate fillers either organic, inorganic or a combination of organic and inorganic are suitable for use. Suitable fillers comprise bone chips, tricalcium phosphate ("TCP"), hydroxyapetite ("HA"), powdered/dried small intestine submucosa (hereinafter "SIS material"), as described in U.S. Pat. Nos. 4,902,508 and 4,956,178, bioglass granules, synthetic polymers, calcium carbonate, calcium sulfate, or collagen. By "immobilize" it is understood that the active compound is associated intimately with the surface. The immobilization may be passive, i.e, by adsorption, or covalent. The particulate has an average diameter of about 10 to about 4000 μm, more preferably about 20 to about 2000 μm.

In addition, the protected mixture may be lyophilized by freezing and removing the water from the mixture in vacuo. Alternative useful means for drying the mixture include critical point drying, vacuum dehydration, and drying agents. Prior to irradiation, the protected mixture comprises preferably less than 4 percent by weight water. More preferably, substantially all uncoordinated water is removed from the mixture prior to irradiation. The significant factor in dehydrating the mixture is that the physiological properties of the biologically active compound are not irreversibly altered. Any significant changes in the characteristics of the biologically active compound due to dehydration should be substantially reversible so that the properties are substantially restored upon reconstruction in the appropriate aqueous medium.

Thus sterilization can be accomplished by radiation with about 1 to about 3 mRad of gamma radiation or electron-beam radiation. If the biologically active composition comprises a biologically active protein or peptide, biological activity can be optimized during sterilization by including in the composition an extraneous protein, for example albumin or gelatin, and a free-radical scavenger (antioxidant), for example propyl gallate, 3-t-butyl-4-hydroxyanisole (BHA) or ascorbic acid. Both the extraneous protein and the free-radical scavenger are added in an amount effective to retard radiation induced degradation of the biologically active peptide. The sterilization is preferably conducted at low temperature, for example =70° C. When a filler is used in the composition with a biologically active peptide or protein, it is advantageous to form a mixture of the biologically active peptide or protein and an extraneous protein such as albumin or gelatin, and coat the filler with that formulation prior to blending the filler into composition.

The biologically active composition, once sterilized, is maintained in a sterile surrounding until use by a caregiver. Conveniently, the sterilized composition may be held in a container sealed or unsealed. Illustrative containers include vials, plates, pouches, jars, etc. Preferably, the container is transparent to both gamma-rays and electron-beams.

The composition and method in accordance with the present invention permit the biologically active compound to retain at least 10 percent of its initial biological activity and thus its physiological activity following the above-described radiation exposure. Preferably, the biologically active compound retains about 50 percent to about 100 percent of its initial biological activity following the above-described radiation exposure.

EXAMPLE 1

In order to determine the viability of proteins treated with irradiation, six sets of samples were prepared and subjected to varying conditions. The control sample and set A samples were prepared as follows: 1.5 ml vials containing 150 mg of porous TCP particles (100–250 μm diameter) were incubated for 3 hours with 0.3 ml of a 25 μg/ml solution of TGF-$\beta_1$ in a 1 percent by weight Gelatin (A100 commercially available from Atlantic Gelatin, Woburn, Mass.), 20 mM Sodium Acetate pH 5.0 buffer. The vials were then rinsed three times with a phosphate buffer solution (hereinafter, "PBS") pH 7.2, and decanted at room temperature. The control samples were stored at 4° C. until assayed. Set A samples were flash frozen in liquid $N_2$, and lyophilized. After lyophilization, the vials of set A were purged with $N_2$, gas sealed, and frozen and irradiated at −70° C. (1 mRad electron-beam radiation).

Samples B, D, E, and F were prepared as follows: 1.5 ml vials containing 150 mg of TCP (100–250 μm) were incubated for 3 hours with 0.3 ml of a 25 μg/ml solution of TGF-$\beta_1$ in 20 mM Sodium Acetate pH 5.0. The vials were then rinsed three times with PBS pH 7.2, and decanted. Sample B was desiccated and irradiated at 4° C. Samples D, E, and F were flash frozen in liquid $N_2$. Following the flash freezing, samples D, E, and F were lyophilized. After lyophilization, the vials of samples D, E, and F were frozen (−70° C.) and remained on dry ice during the irradiation process. The variation of irradiation was B, 2.5 mRad Gamma; D, 1.0 mRad Gamma; E, 2.5 mRad electron-beam; and F, 2.5 mRad Gamma.

After irradiation, the serum extraction of TGF-$\beta_1$ from TCP was conducted as follows: Undiluted horse serum (Sigma Chemical Company, St. Louis, Mo. Cat#H-1270)

with 0.02 percent by weight Sodium Azide was added to TGF-$\beta_1$ TCP. The amount of serum added to the TGF-$\beta_1$ TCP depended upon the TGF-$\beta_1$ concentration. Approximately 1 to 0.4 µg/ml final concentration of TGF-$\beta_1$ was targeted. The serum and TCP were incubated for a minimum of 12 hours (overnight) at room temperature with mixing. To remove TCP fines, the composition was spun in a microfuge at 500×g for one minute. It is understood that additional recovery may be achieved by replacing the serum and repeating the above-described extraction procedure.

The samples were then assayed by an enzyme linked immuno sorbent assay (hereinafter "ELISA") assay to determine biological activity. The TGF-$\beta_1$ Capture ELISA protocol was as follows:

Material

1. Solid Support: Dynatech Immulon II, cat#011-010-3450
2. Coating Buffer: 0.05M Carbonate buffer pH 9.5 $Na_2CO_2$ (5.3 g/L)
3. Capture Mab: Mab <TGF-$\beta_1$>12H5, Genentech, lot #8268-61
4. Wash Buffer: PBS, 0.05 percent by weight Tween 20
5. Detection Mab: Mab <TGF-$\beta_1$> 4A11-HRP Genentech, lot 16904-30
6. Standard: TGF-$\beta_1$, Genentech, used same lot as unknown samples
7. Substrate: Tetramethyl benzidine (TMB), Kirkegaard & Perry Catalog #50-76-100
8. Stop Solution 1M $H_2SO_4$

Procedure

A 96 well microtiter plate was coated with 0.5 µg/ml of Capture Mab in Coating Buffer and held at a temperature of 4° C. overnight at 100 µl/well. The plate was washed with Wash Buffer for 6 cycles in a Titertek Microplate washer 120. The last volume of Wash Buffer was left in the wells. The 96 well plate was incubated for 10 minutes with the Wash Buffer and then emptied of the Wash Buffer. The TGF-$\beta_1$ samples were added to the washed plate and serially diluted in PBS at 100 µl/well. The TGF-$\mu_1$ samples were then incubated for 1 hour at room temperature. The plates were again washed with Wash Buffer for 6 cycles. The Detection Mab was then added to the plate and diluted to approximately 1:2000 in Wash Buffer, 100 µl/well. The plate was then incubated for 1 hour at room temperature. The plates were washed with Wash Buffer for 6 cycles. Next, 100 µl/well of Coating Buffer was added to the plate. The color was allowed to develop for 5 minutes. Then 50 µl/well of Stop Solution was added. The wavelength was read at 450 nm on a Molecular Devices Vmax plate reader.

Optical Density (hereinafter "O.D.") values were curve fit using a log linear regression. Standards of diluted TGF-$\beta_1$ were used to prepare the calibration curve. The results are set out in Table 1.

TABLE 1

| SET | CONDITIONS | RECOVERY % by ELISA) |
|---|---|---|
| Control | 4° C., no irradiation | 100% |
| A | 1.0 mRad Electron-beam, gelatin, $N_2$, –70° C. | 64% |

TABLE 1-continued

| SET | CONDITIONS | RECOVERY % by ELISA) |
|---|---|---|
| B | desiccated; 2.5 mRad γ-radiation | 0% |
| C | 1.0 mRad γ-radiation | 0% |
| D | 2.5 mRad Electron-beam | 0% |
| E | 2.5 mRad γ-radiation | 0% |

The multiple needed to superimpose the regression curve on the calibration curve at an O.D. value in the linear region was used to calculate the unknown concentration.

EXAMPLE 2

In order to determine the relative contributions of various elements of the present invention, the elements were eliminated from the control or "base" conditions.

The base conditions were performed in the following manner: 1.5 ml vials containing 150 mg of porous TCP particulate (100–250 µm diameter) were incubated for 3 hours with 0.3 ml of a 25 µg/ml solution of TGF-$\beta_1$ in a 1 percent by weight Gelatin, 20 mM Sodium Acetate pH 5.0 buffer. The vials were then rinsed three times with 1 ml PBS pH 7.2, and decanted. Control samples were stored at 4° C. until assayed. The samples were flash frozen in liquid $N_2$ and lyophilized. After lyophilization the vials were purged with $N_2$ for 20 seconds, sealed, and frozen at –70° C. The samples remained on dry ice during the irradiation process.

There were five sets of samples compared to the base conditions. Set #1 did not have gelatin present in the formulation. Set #2 was not irradiated in a $N_2$ atmosphere. Set #3 was irradiated at room temperature. Set #4 was subjected to the base conditions, except that it irradiated with 2.5 mRad Gamma. Set #5 was subjected to all of the base conditions, except it was irradiated with 1.0 mRad Gamma.

The extraction and assay procedure was the same as that set forth in Example 1.

The activity of the TGF-$\beta_1$ following irradiation is illustrated in Table 2.

TABLE 2

| Sample | Conditions | % of Activity |
|---|---|---|
| Base | Lyophilized in the presence of gelatin; $N_2$ atmosphere; –70° C., 1 mRad Electron-beam. | 62 |
| 1 | All base conditions except gelatin | 1 |
| 2 | All base conditions except $N_2$ atmosphere | 52 |
| 3 | All base conditions except –70° C. (Room Temperature) | 39 |
| 4 | All base conditions, but used 2.5 mRad Gamma | 38 |
| 5 | All base conditions, but used 1.0 mRad Gamma | 55 |

Referring to Table 2, it is apparent that the addition of the gelatin had the most significant effect on preserving the biological activity of the TGF-$\beta_1$. The gamma radiation caused little greater loss of activity than the Electron-beam radiation.

EXAMPLE 3

In order to explore other conditions where the present invention would be useful, a matrix was made using SIS material and a polymer adhesive. The present invention was utilized to protect TGF-$\beta_1$ in this matrix from gamma sterilization. ELISA was performed as in Example 1. A SIS Material/Polymer Bone filler material was formed from the following reagents:

Reagents

TGF-$\beta_1$: Genentech Lot M1-157, 0.73 mg/ml

Polymer: A polymer as prepared in Preparation 1 below.

Coating Buffer: 20 mM Sodium Acetate, pH 5.0, 1 percent by weight Gelatin.

Free-Radial Scavenger: 0.2 percent by weight N-Propyl Gallate in water.

SIS material: Prepared in accordance with U.S. Pat. Nos. 4,902,508 issued Feb. 20, 1990 and 4,956,178 issued Sep. 11, 1990, supra, comminuted and lyophilized.

PREPARATION 1

Synthesis of Acid-Terminated Polymers

Glassware was dried at 145°–155° C. for 24 hours, fitted with rubber septa, and cooled under a flow of dry nitrogen. Polymerizations were run in 250 mL Erlenmeyer flasks with 24/40 ground glass joints sealed with evacuated glass stoppers wrapped with teflon tape. To a flask (250 mL) containing a magnetic stir bar were added D,L-lactide (18.17 g, $1.26 \times 10^{-1}$ mol), glycolide (14.63 g, $1.26 \times 10^{31}$ $^1$ mol), ε-caprolactone (7.20 g, $6.30 \times 10^{-2}$ mol), glycolic acid (1.66 g, $2.18 \times 10^{-2}$ mol), succinic anhydride (2.19 g, $2.18 \times 10^{-2}$ mol). The flask was purged with nitrogen and heated in a 135° C. constant temperature bath for 20 hours with continuous stirring. At 65 hours of reaction, the temperature was lowered to 110° C. The polymerization was allowed to proceed for 146 hours and was then quenched in an ice-water bath. The product was a ~2,000 g/mole bis-carboxy-terminated PLGC terpolymer.

Analytical titration procedure (2,000 g/mol sample)

To a 125 mL Erlenmeyer flask was added a (~2,000 g/mol) polymer sample (0.30 g –0.40 g). The polymer sample was completely dissolved in THF (50 mL) and water (15 mL) was added to the solution. Phenolphthalein (1 g/100 mL MeOH) (5 drops) was added to the polymer solution, and the flask was placed in an ice bath. The sample was titrated with an aqueous solution of NaOH (0.5047N) to a light pink end point. An average equivalent weight was calculated from the values of at least three titrations.

Bulk polymer titration procedure (2,000 g/mol sample)

To a 1000 mL Erlenmeyer flask was added a (~2,000 g/mol) polymer sample (34.32 g), and the polymer was dissolved in THF (450 mL). The average equivalent weight from the above procedure was used to calculate the exact amount of titrant (85.3 mL, 0.5047N aqueous NaOH) necessary to completely neutralize the polymer sample. This amount was slowly added to the polymer solution as it was stirred in an ice bath. The product PLGC ionomer is dried in vacuo.

The TGF-$\beta_1$ was mixed with the Coating Buffer at 1 ml/100 mg of dry SIS material to form a putty. The mixture was incubated for 1 hour at room temperature. In a separate step, the Free-Radical Scavenger was added to the Polymer and stirred briefly at room temperature until a viscous solution of 4 ml of 0.02 percent by weight Free-Radical Scavenger per gram of Polymer was produced. Then the SIS material/TGF-$\beta_1$ was mixed with the viscous Polymer. The resulting matrix had a final TGF-$\beta_1$ Dose of 5 μg/ml and included SIS material: 33 percent by weight and Polymer:67 percent by weight.

The matrix was then placed in a glass petri dish that could be $N_2$ frozen and shaped so the material could be coated evenly by the Polymer. The matrix was flash frozen with liquid $N_2$ and lyophilized. The samples were packaged for treatment with gamma radiation in a $N_2$ atmosphere sealed foil pack. The matrix was stored at –70° C.

After 2.5 mRad gamma irradiation, the TGF-$\beta_1$ was eluted and analyzed as in Example 1, 13±3% of the original TGF-$\beta_1$ activity could be detected.

EXAMPLE 4

This experiment compared three different free-radical scavengers that can be used in the present invention, propyl gallate, 3-t-Butyl-4-Hydroxyanisole (BHA), and ascorbate.

Procedure: Five groups of 1.5 ml vials containing 150 mg of porous TCP particles (100–250 μm diameter) were incubated for 3 hours with 1 ml of a 12.5 μg/ml solution of TGF-$\beta_1$ in a 1 percent by weight gelatin, 20 mM Sodium Acetate pH 5.0 buffer. The vials were then rinsed three times with 1 ml PBS pH 7.2, and decanted. The positive control group was stored at 4° C. until assayed as in Example 1. Three groups (A, B, and C) of vials were rinsed with 1 ml of the free-radical scavengers (Group A was rinsed with propyl gallate, Group B was rinsed with BHA, and Group C was rinsed with ascotbate) at a concentration of 0.2%, 2%, 2% weight/volume respectively and decanted. The samples were flash frozen in liquid $N_2$, and lyophilized. After lyophilization the vials were purged with $N_2$, sealed, and frozen at –70° C. The samples were on dry ice during the 2.5 mRad gamma irradiation process. The negative control group was TCP and TGF-$\beta_1$ only with no protective elements and irradiated at a 2.5 mRad gamma dose. The results are listed in Table 3.

TABLE 3

| Group | % recovery* |
| --- | --- |
| Positive Control | 100 |
| Negative Control | 0.8 |
| A | 38 |
| B | 36 |
| C | 18.2 |

*% recovery is based on the non irradiated control

Thus, several different free-radical scavengers may be used in the present invention with good results.

EXAMPLE 5

In order to compare in vivo and in vitro biologic activity of the present invention, several treatments were placed in rats. The rat calvaria model was used in these experiments as described in J. P. Schmitz, Z. Schwartz, J. O. Hollinger, B. D. Boyan, *Characterization of Rat Calvaria Nonunion Defects*, Acta Anat, 138, pp. 185–192, (1992). TGF-$\beta_1$ was adsorbed to TCP and implanted into defects in the skulls of rats at various doses without radiation sterilization, and with various protective conditions to preserve activity during gamma sterilization. Bone formation was scored histologically from each of the treatment groups.

Treatment Groups A–G were designed as a dose response curve to calibrate the results of the present invention. A–G were prepared with varying doses of TGF-$\beta_1$, by adsorbing the TGF-$\beta_1$ on to the TCP in 20 mM Sodium Acetate pH 5.0 buffer for 3 hours. The samples were then rinsed three times in saline. This procedure was completed in an aseptic manner, no irradiation was used on groups A–F. Group G received 2.5 mRad Gamma radiation. Groups H and I were prepared the same as Example 2 set #4, except group I did not receive irradiation.

Table 4 summarizes the results:

TABLE 4

| Grp. | Treatment | TGF-$\beta_1$ dose (μg/ml) | Gamma (mRad) | n | Average Bone Score | Std. Dev. |
|---|---|---|---|---|---|---|
| i | Positive control (autologous bone graft) | 0 | 0 | 69 | 2.45 | 0.65 |
| ii | Negative control (TCP granules) | 0 | 0 | 111 | 1.06 | 0.97 |
| A | TCP | 0.006 | 0 | 15 | 1.20 | 1.21 |
| B | TCP | 0.06 | 0 | 24 | 0.83 | 0.82 |
| C | TCP | 0.6 | 0 | 14 | 0.93 | 0.83 |
| D | TCP | 6.0 | 0 | 18 | 1.67 | 1.03 |
| E | TCP | 90 | 0 | 9 | 2.11 | 0.33 |
| F | TCP | 160 | 0 | 42 | 1.76 | 1.14 |
| G | TCP | 270 | 2.5 | 18 | 0.09 | 0.68 |
| H | TCP + protectants | 160 | 2.5 | 12 | 1.67 | 0.49 |
| I | TCP + protectants | 160 | 0 | 12 | 2.00 | 0.00 |

Groups i and ii give the results of the positive and negative controls in the model. Table 4 further shows that even a large dose of TGF-$\beta_1$ (270 μg/ml) had no biological activity after gamma sterilization without protectants. Groups F, H, and I show that the use of the protected mixture gave the same response as an equivalent dose of TGF-$\beta_1$ whether or not the samples were irradiated.

EXAMPLE 6

A putty-like delivery matrix including a polymer, filler, and a biologically active component (TGF-$\beta_1$) was evaluated in vivo in the rabbit radius model.

EXPERIMENTAL DESIGN

Route of Administration

A test article, or the autogenous control, was implanted in the midshaft radial defect.

Overview

A 1.5-cm segment of the right radius was removed, producing a unilateral radial defect. The radial defect was implanted with a test material or a control article, or received no implant, according to group assignment. The incision was closed, and the rabbits were allowed to survive for 8 weeks. At 8 weeks both radii were harvested.

Experimental Procedure

Xylazine/ketamine cocktail was used as the anesthetic agent. The cocktail was made by mixing xylazine (1.42 ml; 100 mg/ml) in ketamine (10 ml; 100 mg/ml). The rabbits were dosed initially at approximately 0.65 ml/kg I.M. (maximum of 3 ml per rabbit). An ear vein was catheterized, and additional anesthesia was given through this catheter at approximately 0.125 of the initial dose, as needed. The right radius was clipped free of hair, then shaved or depilitated and aseptically prepared for surgery.

Surgery

An incision was made mid-shaft over the anterior-medial surface of the right forearm. Soft tissue was reflected to expose the radius. The interosseous ligament between the radius and the ulna was separated, and the periosteum was excised from the radius for approximately 1.7 cm along the mid-shaft. A sterile spatula was placed between the radius and the ulna, and a 1.5 cm segment of the radius was removed, using a saw blade attached to a sagittal saw. The site was liberally irrigated with physiological saline during the ostectomy to prevent overheating of the bone margins.

Experimental Sequence

Each radial defect was filled with one of the test materials or the autogenous graft or was left empty. After the material was molded into position, the soft tissue was reapposed with absorbable suture and the skin was closed with non-absorbable suture.

The amount of material actually implanted was determined by weighing the formulation after preparation, before implanting (using a sterile foil weighing boat or a similar device), and then weighing the material not implanted.

The surgical site was radiographed to document the anatomic placement of the material, and the rabbits were returned to their cages. Buprenorphine hydrochloride (0.15 mg SQ) was administered daily for the first 3 days of recovery for pain.

The rabbits were maintained post surgery for 8 weeks and then terminated with Beuthanasia-D® Special Solution administered intravenously. The right and left radii were removed, and soft tissue was dissected free from these bones. The operated radius was examined histologically for the presence of bone within the defect site (indicating a union) and the presence of cartilage, soft tissue or cracks within the defect site (indicating a possible unstable union or non-union). The observations were scored by a pathologist according to the scale: 0=5 failed, 1=poor, 2=moderate, 3=good, and 4=excellent. The results are set forth in Table 5.

TABLE 5

| TREATMENT | AVERAGE | ST. DEVIATION | n[b] |
|---|---|---|---|
| Autograft (+ control) | 3.4 | 0.5 | 20 |
| Empty (− control) | 0.8 | 1.4 | 20 |
| Polymer[a]/TCP | 0 | 0 | 10 |
| Polymer[a]/TCP/ TGF-$\beta_1$ (γ-sterilized) | 3.8 | 0.3 | 10 |

[a]Polymer of lactide/glycolide/caprolactone with a COONa+ end group (2:2:1; MW 2,000)
[b]n = number of animals This test demonstrated that the compositions of this invention can be used to repair long bones like the radius, which contain marrow, have a rich blood supply, and experience mechanical loading. The amount of bone repaired was consistent with results obtained with conventional delivery matrixes using TGF-$\beta_1$ that had not been gamma sterilized.

EXAMPLE 7

The present invention was formed in solution with no support matrix.

A solution of TGF-$\beta_1$ at 0.8 µg/ml in 2.5 percent by weight gelatin solution, 0.2 percent by weight N-propyl gallate, in 20 mM Sodium Acetate was produced. Then, 0.5 ml of the solution was placed in 0.5 ml micro-centrifuge tubes. Six tubes were lyophilized and the solution in the other six tubes remained in solution. These tubes were frozen and packaged in $N_2$ atmosphere. Half of each set of samples was irradiated with 2.5 mRad of Gamma while on dry ice, and stored at −70° C. ELISA was performed as in Example 1 and the results are set out in Table 6.

TABLE 6

| Gamma samples TGF-$\beta_1$ no TCP | | | |
|---|---|---|---|
|  | n n | % recovery | Standard Deviation |
| Solution | 3 | 39 | 6% |
| Solution 3 no gamma | 68 | 7% |  |
| Lyophilized no gamma | 3 | 103 | 66 % |
| Lyophilized | 3 | 26 | 9% |

Although the invention has been described in detail with reference to certain preferred embodiments variations and modifications exist within the scope and spirit of the invention as described and defined in the following claims.

What is claimed is:

1. A method for sterilizing a biologically active compound and optimizing retention of physiological activity of said compound, the method comprising the steps of forming a mixture comprising the biologically active compound, and an extraneous protein, cooling the mixture to a temperature sufficient to substantially freeze and immobilize said mixture, and irradiating the immobilized mixture with gamma or electron beam radiation for a time sufficient to substantially sterilize the biologically active compound.

2. The method of claim 1, wherein the mixture is irradiated with about 1 to about 3 mRad of gamma radiation.

3. The method of claim 1, wherein the immobilized mixture is irradiated with about 2.5 mRad of gamma radiation.

4. The method of claim 1, wherein the mixture is irradiated with about 1 mRad to about 3.0 mRad of electron-beam radiation.

5. The method of claim 1, wherein the mixture is immobilized on a solid particulate with an average diameter of about 20 µm to about 2000 µm.

6. The method of claim 5, wherein the solid is tricalcium phosphate.

7. The method of claim 6, wherein the substrate is a particulate substrate.

8. The method of claim 1, wherein the immobilized mixture is irradiated with electron-beam radiation.

9. The method of claim 6, wherein the step of immobilizing the mixture on the substrate comprises the step lyophilizing the mixture.

10. The method of claim 1, wherein the mixture is cooled to about −70° C. and the temperature of the mixture is maintained at about −70° C. during irradiation.

11. The method of claim 1, wherein the extraneous protein is selected from the group consisting of gelatin and albumin.

12. A method for sterilizing a composition comprising a biologically active biopolymer with gamma or electron-beam radiation while preserving at least 10 percent of the activity of the biopolymer in said composition, the method comprising the steps of forming a protected mixture comprising the biologically active biopolymer, an extraneous protein, and a free-radical scavenger, and irradiating the protected mixture with about 1 to about 3 mRad of gamma or electron-beam radiation.

13. The method of claim 12, wherein the extraneous protein is selected from the group consisting of gelatin and albumin.

14. The method of claim 13, wherein the protected mixture is irradiated with about 2.5 mRad of gamma radiation.

15. The method of claim 12, wherein the biologically active biopolymer is a bone growth factor.

16. A biologically active composition that exhibits an initial biological activity prior to radiation exposure of about 1 to about 3 mRad of gamma or electron-beam radiation and that retains at least 10 percent of the initial biological activity following such radiation exposure, the composition comprising a mixture comprising about $10^{-5}$ to about 2.5 weight percent of a biologically active compound, about 0.01 to about 10 weight percent of a free-radical scavenger, and about 1 to about 70 weight percent of an extraneous protein.

17. The composition of claim 16, wherein the biologically active biopolymer is a peptide or protein.

18. The composition of claim 17, wherein the extraneous protein is gelatin.

* * * * *